(12) United States Patent
Stone

(10) Patent No.: US 6,913,580 B2
(45) Date of Patent: Jul. 5, 2005

(54) METHOD OF BODY FLUID SPECIMEN COLLECTION

(75) Inventor: Benjamin Curtis Stone, 629 S. Johnson St. Apt. #3, Iowa City, IA (US) 52240

(73) Assignee: Benjamin Curtis Stone, Iowa City, IA (US)

( * ) Notice: Subject to any disclaimer, the term of this patent is extended or adjusted under 35 U.S.C. 154(b) by 125 days.

(21) Appl. No.: 10/055,290

(22) Filed: Jan. 23, 2002

(65) Prior Publication Data

US 2003/0013991 A1 Jan. 16, 2003

Related U.S. Application Data

(60) Provisional application No. 60/263,370, filed on Jan. 23, 2001, and provisional application No. 60/306,643, filed on Jul. 19, 2001.

(51) Int. Cl.[7] .................................................. A61B 5/00
(52) U.S. Cl. ...................................... 600/577; 600/583
(58) Field of Search ................................ 600/573, 576, 600/577, 579, 583

(56) References Cited

U.S. PATENT DOCUMENTS

| 4,676,256 A | * | 6/1987 | Golden ........................ 600/575 |
| 5,429,610 A | * | 7/1995 | Vaillancourt ................. 600/573 |
| 5,577,513 A | * | 11/1996 | Van Vlasselaer ............ 600/578 |

* cited by examiner

Primary Examiner—Eric F. Winakur

(57) ABSTRACT

In one aspect of the invention, a method of fluid specimen collection comprises the steps of: preparing a site for puncture using an antiseptic; piercing the prepared puncture site using a fluid collection needle; collecting a first body fluid specimen using a device for collecting the first body fluid specimen; collecting a second body fluid specimen using a device for collecting the second body fluid specimen and; selecting the second body fluid specimen for a diagnostic test of a kind that detects the presence of organisms in the second body fluid specimen. In another aspect of the invention, a vessel for collecting, transporting, and transferring a body fluid specimen comprises: a hollow body having a first and second end; a first seal at said first end; a plunger disposed within said hollow body between said first end and said second end; said plunger providing a second seal; a plunger lock coupled to said plunger; said plunger lock being configured to selectively maintain said plunger at said second end when at least a portion of said hollow body between said first seal and said second seal is at least partially evacuated; said plunger lock can further be configured to release said plunger, thereby allowing said plunger to move toward said first seal within said body.

17 Claims, 10 Drawing Sheets

METHOD OF BODY FLUID SPECIMEN COLLECTION

PARENT CASE TEXT

This application claims benefit of provisional application No. 60/263,370 filed Jan. 23, 2001 and provisional application No. 60/306,643 filed Jul. 19, 2001, the contents of which are incorporated herein.

CROSS REFERENCE TO RELATED APPLICATIONS

N/A

STATEMENT REGARDING FEDERALLY SPONSORED RESEARCH OR DEVELOPMENT

N/A

REFERENCE TO A MICROFICHE APPENDIX

N/A

DISCUSSION OF THE PRIOR ART

There are a number of known methods for collecting blood/body fluid specimens for culturing. This section discusses prior art methods for collecting blood specimens into evacuated culture vessels. Of these, there are methods that collect directly into the culture vessels and those that collect into an intermediate prior to inoculation of the culture vessels.

The methods of the prior art must deal with two interfering factors in order to avoid false negative and false positive culture results. The first of these is contamination of the blood specimen, which frequently leads to false positive results with an organism recovered by subculture and isolation. It is widely accepted that the most common sources of contaminants are the skin flora organisms of the patient or blood collector from the venepuncture site, and organisms from the contact surfaces of equipment used to collect or transfer the blood specimen. Prior art attempts to control contamination have centered on using preparatory antiseptics to limit the number of potential contaminants from the venepuncture site, and additional antiseptics to treat the contact surfaces of the collection and transfer equipment. These techniques require relatively great effort on behalf of the blood collector in order to be effective. First, for preparatory antiseptics such as povidone-iodine, a drying time of one to two minutes is needed before the antiseptic becomes active. Therefore, venepuncture prior to this active stage is more likely to include contaminants. Second, with any preparatory antiseptic, re-palpation of the venepuncture site after application of the antiseptic also increases the probability of contaminant inclusion with the blood specimen. Because palpation is the primary tool used by blood collectors to locate a vein and due to the waiting time required for some preparatory antiseptics, re-palpation does occur with some frequency. Third, prior art methods that draw blood directly into evacuated culture vessels are subject to some frequency of contact with the surfaces of culture vessels after they have been treated with antiseptics.

The second interfering factor is blood specimen irregularity. A less frequently recognized factor, it can lead to false negative and false positive results. Current systems for detecting growth of organisms in culture vessels are based on monitoring the rates of change in the culture vessel's internal environment factors such as carbon dioxide content, pH change, or fluorescence. The rate of these changes is generally dependent upon the volume of blood used to inoculate the culture vessels. Low specimen volumes containing a true pathogenic organism may require substantially longer periods of time to show a detectable rate of change in the monitored factor, thereby delaying detection of the organism or providing a false negative result. High specimen volumes often including relatively higher concentrations of leukocytes are known to cause false positives by providing increases in carbon dioxide gas production. In addition, these types of false positive results may also lead to false negative results. This occurs when an anaerobic culture vessel is inappropriately identified as positive and a subculture is performed. The subculture requires that a cannula be used to access the blood specimen, thus introducing ambient air into the culture bottle. Ambient air contains oxygen, which will greatly hinder the growth of obligate and facultative anaerobic organisms, thus potentially resulting in a false negative.

Some prior art methods attempt to control blood specimen volume by providing a graduation on the sides of culture vessels. These graduations generally have no start or end point, and because the vessel contains a liquid media, it is difficult to monitor the volume of blood used to inoculate. In addition, bubbles on the surface of the liquid media disrupt the meniscus and further hinder proper collection. Due to this, prior art methods that draw directly into the culture vessels are more prone to inoculating volume irregularity. Prior art methods that use an intermediate such as a syringe also incur some volume irregularity due to the relatively large size of the recommended inoculating volume. Many evacuated culture vessels recommend an inoculating volume of 10 ml per vessel. Because this type of method uses aerobic and anaerobic culture vessels, a total of 20 ml is required for culturing. If additional tests are ordered the size of the syringe used for collection must also increase. Some collectors choose to use less volume to inoculate the culture vessels instead of using larger syringes. And because inoculating volumes are rarely monitored, this leads to irregularity.

False positive results that recover an organism and false negative results are the two most precarious failures of a detection system. Both can lead an increased rate of mortality for the patient, and more frequently to increased length of hospital stay and cost. Therefore, for the reasons discussed above it is important to develop a method for collecting a blood specimen for culturing that is less prone to blood collector error.

SUMMARY

This invention provides a method and manufactures for collecting a specimen of blood or body fluid, from herein to be referred to as body fluid specimens only, from a patient for subsequent diagnostic testing. In one aspect of the invention, the method comprises the steps of:

a. piercing the skin with a fluid collection needle, of the kind having one beveled end for piercing the skin, and another for piercing a self-sealing stopper;
b. collecting a first body fluid specimen using an evacuated specimen tube that is sterile throughout;
c. and collecting additional body fluid specimens, from herein to be referred to as the second body fluid specimen, using an evacuated culture vessel of the kind containing a liquid media.

Collecting the first body fluid specimen with the sterile evacuated specimen tube will also be referred to as contaminant redirection. The purpose of this technique is to remove potential contaminants from the internal surfaces of the collection needle by establishing body fluid flow, without contaminating the collection needle. A step of treating the site to be pierced with preparatory antiseptics such as iodophors, iodine tinctures, or chlorhexidine, may precede the first step (step a) of this method if it is found to be more effective in practice. But the preferred method should allow for re-palpation of the site without adding contaminants to the second body fluid specimen.

In a preferred embodiment of the method, a body fluid collection vessel is used to collect the second body fluid specimen. The body fluid collection vessel has properties that allow for collection of the body fluid specimen as well as transfer of the body fluid specimen to an evacuated culture vessel. The body fluid collection vessel comprises:
a. a hollow body with an open end and a partially closed end;
b. a self-sealing stopper that seals the open end;
c. an internal plunger that seals the other end;
d. a plunger lock that reversibly locks to the internal plunger through the partially closed end of the body.

When assembled, with the internal plunger reversibly locked to the plunger lock and the stopper sealing the open end, this vessel is to be evacuated during manufacture in a manner similar to evacuated specimen tubes and sterilized. It is also preferred that fluid collection vessels and the sterile evacuate specimen tube be packaged together as a kit for collecting blood specimens. The method for collecting the second body fluid specimen with this kit comprises the steps of:
a. piercing the skin of a patient using the body fluid collection needle;
b. collecting the first body fluid specimen using the sterile evacuated specimen tube;
c. collecting the second body fluid specimen using the fluid collection vessels.

This method has the benefit of conforming more closely to current multiple sampling methods used by blood collectors, given that the collection vessels are designed to collect using the same vacuum principles as evacuated specimen tubes.

In this embodiment, the collection vessel should contain an additive that preserves the second body fluid specimen for culturing. Sodium polyanetholesulfonate is a likely candidate, as it is shown by the prior art to be an anticoagulant that does not remove essential elements from the body fluid, such as calcium ions, and also has anticomplement system activity. With this additive, the second body fluid specimen may be transported to a workstation where it will be transferred to the evacuated culture vessel. This is performed using a transfer device comprising:
a. a transfer needle having a first and a second end for piercing self-sealing stoppers;
b. a first needle shield to prevent accidental needle stick with the first end of the transfer needle;
c. a second needle shield to prevent accidental needle stick with the second end of the transfer needle.

The transfer device is to be used in a method of transfer comprising the steps of;
a. unlocking the plunger lock from the internal plunger of the collection vessel;
b. piercing the self-sealing stopper of the collection vessel using the first end of the transfer device;
c. piercing the self-sealing stopper of the evacuated culture vessel using the second end of the transfer needle.

This method allows for adequate, safe, and simplified transfer of the second body fluid specimen from the collection vessel to the evacuated culture vessel. This method also provides a checkpoint at which the volume of the second body fluid specimen can be monitored prior to and during inoculation of the evacuated culture vessel.

DETAILED DESCRIPTION OF THE PREFFERED EMBODIMENTS

Figure 1:
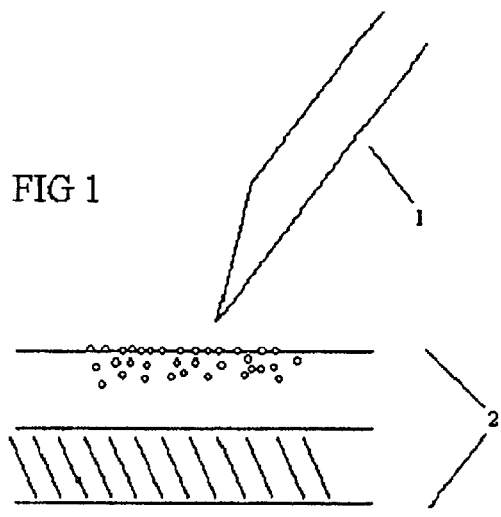
FIG. 1—This is a view showing a cross section of the skin and vein of a patient prior to piercing with the collection needle, showing potential contaminants (black dots) residing on the surface as well as deeper within the layers of the skin.
Figure 2:
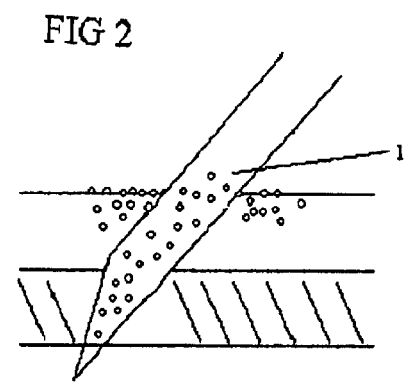
FIG. 2—This is the view showing a cross section of the skin and vein of a patient of after piercing with the body fluid collection needle of FIG. 1, also in cross section, showing the potential contaminants contained within the collection needle.
Figure 3:
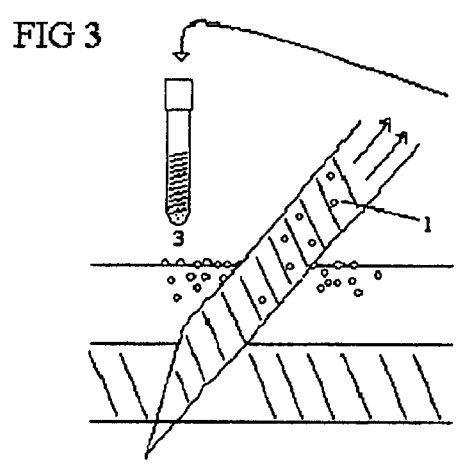
FIG. 3—This is the view showing a cross section of the skin and vein of a patient after piercing with the body fluid collection needle of FIG. 1, also in cross section, with the sterile evacuated specimen tube applied to the opposite end of the collection needle in order to establish body fluid flow and collect potential contaminants. Shown such that the sterile evacuated specimen tube is miniaturized and the fluid collection needle is enlarged relative to one another.
Figure 4:
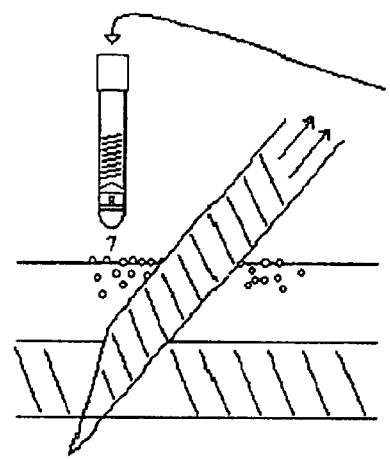
FIG. 4—This is the view showing a cross section of the skin and vein of a patient after piercing with the body fluid collection needle of FIG. 1, also in cross section, with the sterile evacuated specimen tube of FIG. 3 removed and showing the collection vessel applied to collect the second body fluid specimen. Shown such that the collection vessel is miniaturized and the fluid collection needle is enlarged relative to one another.
Figure 5:
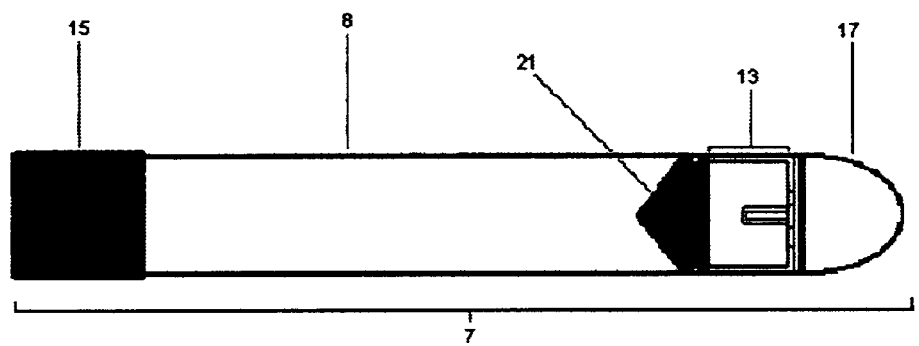
FIG. 5—This is a side view of the collection vessel.

The embodiments of this invention require the following devices in order to collect a blood/body fluid specimen for diagnostic testing, e.g. blood culturing:

a. a fluid collection needle for piercing the skin of a patient, having a first and a second end;
b. a device for collecting a first body fluid specimen;
c. a device for collecting a second body fluid specimen;

As used herein, the phrase "body fluid specimen" means any fluid that comes from the body of a living organism, but especially blood coming from a human.

The fluid collection needle used to pierce the skin of a patient should be of the kind that allows for collecting multiple specimens of body fluid when assembled with either of the two devices of (b) and (c). Fluid collection needles suitable for this invention include, but are not limited to, fluid collection needles 1 of the kind having a first beveled needle 1 for piercing the skin of a patient 2 and a second beveled needle for piercing self-sealing stoppers. This type of collection needle 1 also has plastic threading that corresponds to threading of a conventional needle holder. The conventional needle holder is of the kind having a hollow cylindrical body, having an open end that allows entry of specimen tubes and a partially closed end that is perforated by an opening that contains threading that corresponds to the threading of a fluid collection needle. Both of these devices are well known in the art and are commonly used along with evacuated specimen tubes to collect body fluid specimens. These devices also often carry a means of preventing accidental needle sticks.

Other devices suitable for collecting multiple body fluid specimens include winged collection sets. Winged collection sets are of the kind having a beveled needle, the first end of the fluid collection needle, for piercing the skin of a patient connected to a tube that communicates with the beveled end. Winged collection sets of this type also have a female luer-type connector, allowing for its attachment to a syringe or a luer-type adapter of the kind having a connector for the female luer-type adapter, a beveled needle, the second end of the fluid collection needle, and threading that corresponds to the threading of a conventional needle holder. This type of an assembly is also well known in the art and is commonly used to collect blood specimens. Winged collection sets also commonly carry a means to prevent accidental needle sticks.

Many other devices are capable of piercing the skin of a patient and allow for collecting multiple sampling of body fluid sources, and this disclosure should not be construed so as to be limited to the devices listed.

Regardless of the type of device used to pierce the skin, it must allow for multiple sampling of body fluid specimens. As used herein, the term "multiple sampling" means a process in which a first individual specimen is obtained by assembly of the fluid collection needle with a first device for collecting a specimen of body fluid, followed by removal of the first device for collecting body fluid, followed by assembly of a second device for collecting body fluid with the fluid collection needle in order to collect a second individual body fluid specimen. The latter half of this process may continue with a plurality of devices for collecting body fluid until the desired number of specimens has been collected.

The device for collecting the first body fluid specimen must be capable of collecting a body fluid specimen when assembled with the fluid collection needle without contaminating the second end of the fluid collection needle.

One device that is suitable for collecting the first body fluid specimen 4 is a sterile evacuated specimen tube 3 of the kind having a body formed of materials including, but not limited to polyvinyl chloride or polyethylene terephthalate, closed at one end and open at the other. The open end is closed with a self-sealing stopper and the device is evacuated using manufacturing methods well known in the art. In this preferred embodiment, the sterile evacuated specimen tube 3 must also be sterilized and packaged to maintain sterility using techniques well known in the art. The sterilization techniques include, but are not limited to gamma irradiation, electron beam exposure, and autoclave.

The device for collecting the first body fluid specimen may contain no additives, but may also contain additives that include, but are not limited to ethylenediamine tetraactetic acid (EDTA). In this case, the EDTA additive in the proper concentration would allow a body fluid specimen of whole blood to be used in many diagnostic tests such as a complete blood count (CBC). Other types of devices capable of collecting a body fluid specimen when assembled to the fluid collection needle without contaminating the second end of the fluid collection needle can be used, and this disclosure should not be construed so as to be limited to the devices described.

Regardless of what type of device is used to collect the first body fluid specimen, the assembly and removal of the device for collecting the first body fluid specimen with the fluid collection needle must not contaminate the second end of the fluid collection needle. As used herein, the term "contaminate" means to add or include a sufficient quantity of organisms to a solid or fluid material such that their eventual inclusion in a body fluid specimen would potentially make the organisms indistinguishable from a true pathogen upon subsequent diagnostic testing of the body fluid specimen. This definition will be applied accordingly to terms including "contaminating", "contamination", and "contaminant".

As used herein, the phrase "second body fluid specimen" means body fluid specimens collected after the first body fluid specimen, and may include a plurality of individual body fluid specimens collected by a plurality of devices similar to the device for collecting the second body fluid specimen when assembled with the device for puncturing the skin.

One device suitable for collecting the second body fluid specimen is an evacuated culture vessel 6 of the kind having: a glass or plastic hollow cylindrical body closed at one end and open at the other; the open end closed with a self-sealing stopper; having a liquid media contained within the hollow cylindrical body; evacuated using methods well known in the art; sterilized and packaged to maintain sterility. This type of evacuated culture vessel 6, well known in the art, commonly has a means for responding to changes in the internal environment of the culture vessel and is used in an automated system for detecting those responses. Others have no means for responding to changes and use an invasive method for monitoring changes in the internal environment of the evacuated culture vessel. Other types of evacuated culture vessels are suitable for collecting the second body fluid specimen and this disclosure should not be construed to include only those listed.

Another suitable device for collecting the second body fluid specimen is a sterile evacuated specimen tube containing the additive SPS. This type of sterile evacuated specimen tube is well known in the art.

Another suitable device for collecting the second body fluid specimen is a collection vessel. Three preferred embodiments for this collection vessel are given. In all the embodiments the second body fluid specimen is transferred to an evacuated culture bottle including but not limited to the types previously listed, using a transfer device. These embodiments are preferred because they allow for a simplified collection of the second body fluid specimen using a method to be described later.

Figure 6:
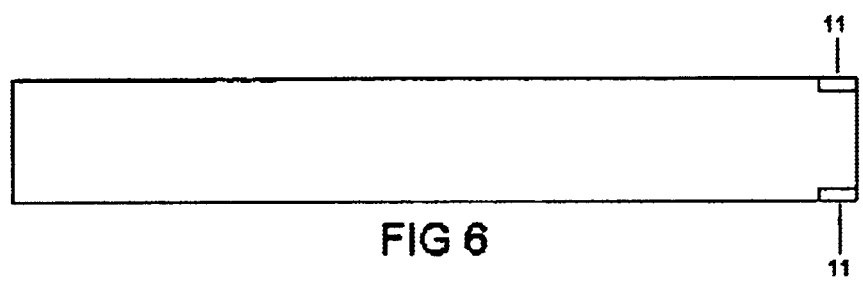
FIG. 6—This is a side view of the collection vessel body, showing the body ridges aligned so that on is closest and the other is furthest from the viewer.
Figure 7:
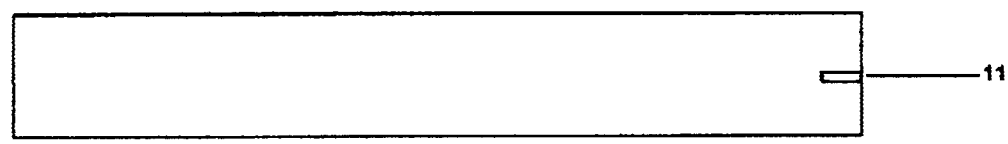
FIG. 7—This is a side view of the collection vessel body of FIG. 6 rotated 90 degrees, showing the body ridges aligned such that they are equidistant from the viewer.
Figure 8:
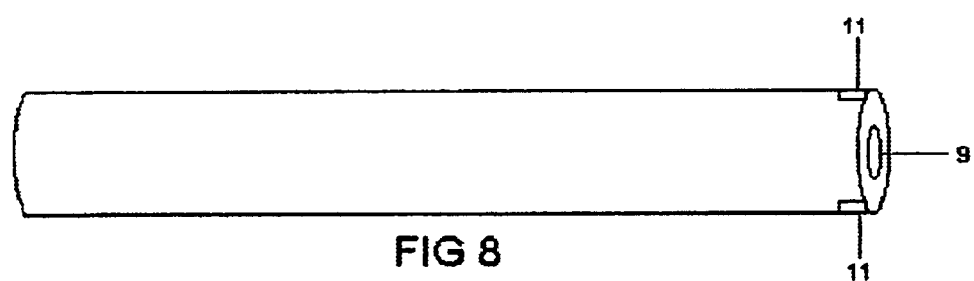
FIG. 8—This is a perspective view of the collection vessel body of FIG. 6, turned to display the partially closed end and the vessel body foramen.
Figure 9:
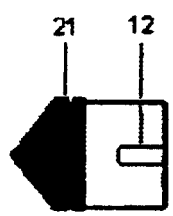
FIG. 9—This is a side view of the vessel plunger, showing the plunger grooves aligned so that one is closest and the other is furthest from the viewer.
Figure 10:
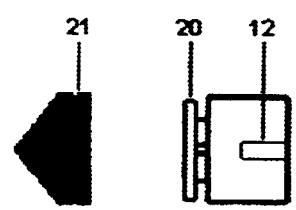
FIG. 10—This is a side view of the vessel plunger of FIG. 9, showing the rubber seal removed from the plunger to display the rubber seal hold.
Figure 11:
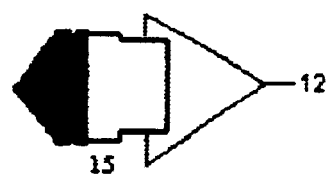
FIG. 11—This is a side view of the plunger of FIG. 9 rotated 90 degrees, showing the plunger grooves aligned such that they are equidistant to the viewer.

The first preferred embodiment comprises: a hollow body having a first and second end; a first seal at said first end; a plunger disposed within said hollow body between said first end and said second end; said plunger providing a second seal; a plunger lock coupled to said plunger; said plunger lock being configured to selectively maintain said plunger at said second end when at least a portion of said hollow body between said first seal and said second seal is at least partially evacuated; said plunger lock can further be configured to release said plunger, thereby allowing said plunger to move toward said first seal within said body;

A detailed description of the first preferred embodiment for the collection vessel will be given here. The hollow body 8 is preferably of a cylindrical shape having a diameter of approximately 1.4 cm and made of such materials including, not limited to, polyvinyl chloride or polyethylene terephthalate. The length of the body 8 may vary, but should provide the completed vessel 7 with a capacity of roughly 10 ml. One end, the first end, of the hollow body will be open having a diameter that is uniform with the rest of the body and the other end, the second end, will have an enclosure made of the same plastic material used to form the body 8. The enclosure will be perforated by an opening, a vessel body foramen 9, having a diameter of 0.8 cm, providing access to the internal space of the body. The diameter of the foramen 9 may vary, but should allow for passage of the plunger lock's male screw 10. The body 8 will also have ridges 11 made of the same material as the body 8 and continuous with the body 8. The ridges 11 should have length of 0.5 cm and a width of 0.2 cm and oriented as they are illustrated in FIGS. 6, 7, 8. The number and dimensions of the ridges 11 may vary, but they should be of the proper dimensions to allow assembly of the ridges 11 with the plunger grooves 12 and of sufficient number to prevent rotation of the plunger 13 when the ridges 11 are assembled with the grooves 12. In this embodiment, the minimum number of ridges 11 and grooves 12 is one of each, but multiples of both are preferred, and equal numbers of the two 11, 12 are necessary.

The first seal at the open end of the body will be a stopper 14, preferably made of an elastomer that is self sealing. The process of making the self-sealing stopper 14 is well known in the art. The stopper 14 should be of dimensions that allow entry of part of the stopper into the open end of the body, thus sealing it, and prevent entry of the other part of the stopper in order that the stopper 14 is held in place at the open end.

A stopper cap 15 is formed of a body in the shape of a hollow cylinder, open at one end and partially closed at the other. The body should have a diameter of roughly 1.6 cm, sufficient to allow it's placement over the assembled stopper 14 and vessel body 8. The partially closed end has a plastic enclosure that is continuous with the rest of the stopper cap's body and is perforated by a opening that contains threading forming the stopper's female screw 16. The stopper's female screw 16 may accommodate the plunger lock 17 during transport to prevent contamination of the stopper 14. Therefore, it is preferable that the stopper's female screw 16 has dimensions and threading that closely match those of the plunger's female screw 18 that will accommodate the plunger lock's male screw 10 during collection. The stopper cap 15 may be manufactured using processes for manufacturing plastic structures well known in the art. The stopper cap 15 is not absolutely necessary to general function, but the presence of the cap 15 is preferred because it acts as a guide for the second end of the fluid collection needle and provides a second use for the plunger lock 17 following collection of the second body fluid specimen.

Figure 12:
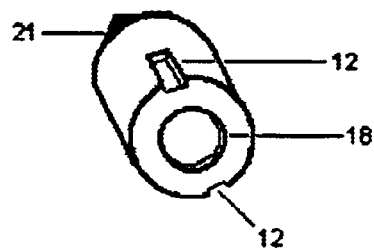
FIG. 12—This is a perspective view of the plunger of FIG. 9, turned to display the plunger's female screw and plunger grooves.

The vessel plunger 13 should have a cylindrical body having a diameter of roughly 1.3 cm to allow for its entry into the vessel body 8 and to allow it to move freely within the vessel body 8 when not held in place by the plunger lock 17. Continuous with the body at one end will be the rubber seal hold 20. In the first embodiment the rubber seal hold 20 will be a plastic disk over which fits a rubber seal 21, the second seal. This type of attachment is well known in the art of making syringes. The strength of the attachment may also be augmented using an adhesive in order to prevent disengagement of the rubber seal 21 from the hold 20 during assembly. The rubber seal 21 provides the plunger with means for sealing with the vessel body 8. At the other end, the plunger 13 will also contain the plunger grooves 12. As illustrated in FIGS. 9, 10, 11, and 12, the grooves 12 correspond in dimensions and orientation to the body's ridges 11, such that when the grooves 12 and ridges 11 are assembled the plunger 13 will not move rotationally. As with the ridges 11, the grooves 12 may vary in number, but at least one is needed for this embodiment. This end of the plunger will also contain the female screw 18 of the plunger as shown in FIG. 12. The plunger's female screw 18 should have a diameter of 0.7 cm and a depth of 0.4 cm into the plunger's body. These dimensions may vary, but must correspond to the dimensions of the plunger lock's male screw 10.

In the first embodiment, the plunger lock will have a male screw 10 with dimensions that correspond to the plunger's female screw 18, having a diameter of 0.7 cm and a depth of 0.4 cm. The male screw's threading should be of the dimensions and spacing such that it can be engaged and translated into the plunger's female screw 18 and also the stopper cap's female screw 16 using hand rotation. The remaining body of the plunger lock can vary in shape in size. In this specific embodiment, it is a dome that has a similar shape to the bottom portion of an evacuated specimen tube. The plunger lock's male screw 10 and body may be made of materials such as nylon, but is not limited to this material.

Figure 13:
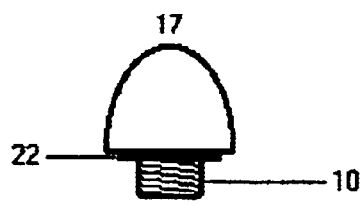
FIG. 13—This is a side view of the vessel's plunger lock showing the lock's male screw and elastomeric sealing ring.
Figure 14:
FIG. 14—This is a side view of the vessel stopper.
Figure 15:
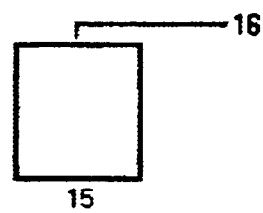
FIG. 15—This is a side view of the stopper cap.
Figure 16:
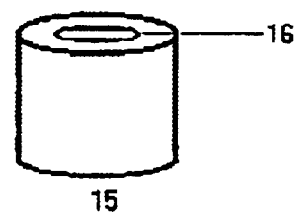
FIG. 16—This is a perspective view of the stopper cap of FIG. 15, turned to display the cap's female screw.

The plunger lock may also have a ring 22 made of an elastomer that surrounds the base of the male screw 10 as in FIG. 13. In the event that the plunger 13 is insufficient to seal the vessel body 8 when it is evacuated for an adequate period of time, the plunger lock's ring 22 will help maintain the evacuated state by sealing the partially closed end of the body.

Assembly of the collection vessel 7 requires that the plunger 13 be placed within the vessel body 8, with the plunger's rubber seal 21 nearest to the open end of the body, and the plunger's female screw 18 nearest to the second end of the body. The plunger 13 should then be pushed back towards the second end and rotated until the plunger grooves 12 engage and translate into the body ridges 11. The plunger lock 17 should then be engaged and translated into the plunger 13 by rotation. The stopper 14 should then be placed into the open end of the vessel body, thus sealing the body 8. The stopper cap 15 should then be placed over the stopper 14, completing the assembly of the collection vessel 7.

In order to collect the second body fluid specimen, this embodiment of the collection vessel 7 must be evacuated during manufacture using methods well known in the art. This will provide a region of relatively lower pressure within the collection vessel 7, such that piercing of the stopper 14 using the second end of the fluid collection needle will allow for transfer of fluids in communication with the first end of the fluid collection needle.

In the first embodiment it is preferred that the completed vessel 7 also contain the additive SPS in order that a second body fluid specimen of blood not coagulate during transport, and that the complement system of the blood not degrade organism that might be contained in the specimen.

A second preferred embodiment for a device for collecting the second body fluid specimen will be described here. This device for collecting the second body fluid specimen is also a collection vessel, but comprising: a hollow body having a first and second end; a first seal at said first end; a plunger disposed within said hollow body between said first end and said second end; said plunger providing a second seal; a plunger lock coupled to said plunger; said plunger lock being configured to selectively maintain said plunger at said second end when at least a portion of said hollow body between said first seal and said second seal is at least partially evacuated; said plunger lock can further be configured to release said plunger from said second end, thereby allowing said plunger and said plunger lock to move toward said first seal within said body;

This second preferred embodiment of the collection vessel 23 is preferred because it may be more easily assembled during manufacture. The collection vessel's body 24 should be of dimensions similar to that of the first embodiment for a collection vessel 8 described above and may be made of equivalent materials. However, the body in this embodiment need not have the ridges 11, as the plunger will not have corresponding grooves 12. The collection vessel body 24 will have an open end and a partially closed end. The partially closed end will have an enclosure, continuous with the body, perforated by an opening 25 of rectangular shape. The dimensions of the opening 25 should be roughly 0.7 cm by 0.3 cm. The open end will be sealed with a sealing means, comprising in this embodiment a stopper 39 of material and dimensions equivalent to the stopper 14 described in the first embodiment.

In this embodiment the plunger will have a cylindrical body of dimensions and formed of materials equivalent to the plunger body of the first embodiment. The plunger will also have at one end a rubber seal hold equivalent to the hold 21 of the first embodiment that fits over a rubber seal 40. At the other end, the plunger will have the means for locking with the body 24. In this embodiment, the plunger lock will be a T-shaped lock 27 made of the same material as the plunger body and continuous with the plunger body. The T-shaped lock 27 will have dimensions that allow for its passage through the opening 25 of the partially closed end.

Once the lock 27 passes through the opening 25, the lock 27 will be turned 90 degrees to anchor the plunger in position. A number of shapes for the lock 27 and opening 25 would be suitable for anchoring the plunger in position in such a manner. This description should not be construed to limit this aspect of the embodiment to that which is described.

To complete assembly of the collection vessel 23, the stopper 41 will be placed in the open end of the body, sealing the vessel 23. The assembly 23 will also be evacuated using processes well known in the art. Means for ensuring the seal of the body 24 by the rubber seal 40 may also be included in any of the embodiments. Gels, waxes, or solid media, in small amounts may be placed at the margins where the rubber seal 40 contacts the vessel body 24 to ensure that vacuum is preserved in the vessel for longer term storage. These means for ensuring the seal of the body 24 and rubber seal 40 should be employed if quality control for mass manufacturing finds that tubes have lost vacuum after unreasonably short term storage.

This embodiment 23 should also contain the SPS additive equivalent to the additive described in the first embodiment 7.

A third embodiment for the collection vessel will also be described here. This embodiment is preferred because it uses a transfer needle as opposed to the transfer device 29 in a method of transfer the second body fluid specimen as will be described later.

The third embodiment comprises: a hollow body having a first and second end; a first seal at said first end; a plunger disposed within said hollow body between said first end and said second end; said plunger providing a second seal; a plunger lock coupled to said plunger; said plunger lock being configured to selectively maintain said plunger at said second end when at least a portion of said hollow body between said first seal and said second seal is at least partially evacuated; an airtight junction that interrupts said hollow body forming a first section and second section; said first section having said first seal; said second section having said plunger and said plunger lock; said plunger lock can further be configured to release said plunger, thereby allowing said plunger to move toward said airtight junction within said body; said airtight junction configured to allow for separation of the first and second section and coupling of a transfer needle to said second section.

This embodiment will have a body 30 that has similar dimensions and is made of materials equivalent to the collection vessel embodiments described above. However, the open end of the body will be partially closed by a female luer-type fitting 31. This embodiment comprises a plunger 42 that anchors to an opening or to a plunger lock 43, all of which may be equivalents to the plungers, openings, and plunger locks described in the first and second collection vessel embodiments 7,23.

This embodiment also uses an adapter, the second section, having a hollow body 32 with an open end and a partially closed end. The length of the body 32 will be roughly 2.0 cm with an open end and a partially closed end. The open end will be sealed with a stopper 44 equivalent to the stopper 14 of the first embodiment for a collection vessel. The partially closed end will have a male luer-type fitting 33.

In this embodiment, the adapter will be assembled with the other elements of the collection vessel having been assembled as described. This completed collection vessel will then be evacuated using processes well known in the art.

This embodiment should contain an SPS additive that is equivalent to the additive described in the first embodiment.

The transfer device must be capable of transferring the second body fluid specimen from a prepared collection vessel to the evacuated culture vessel. One device that is suitable for transferring the second body fluid specimen is the fluid collection needle 1 described above. Having a first and second needle, both with beveled ends, communication of the first end with the evacuated culture vessel, and the second end with the prepared collection vessel containing the second body fluid specimen would adequately transfer the second body fluid specimen. Other types of transfer devices may be suitable for transferring the second body fluid specimen to the evacuated culture vessel and this disclosure should not be construed to limit the possibilities to those listed.

The transfer device described here is to be used in a method described later using the first or second embodiments of the collection vessel and comprises: a fluid transfer means having a first and second end; a first means for shielding the first end of the fluid transfer means, having a body that is bound to a second means for shielding the fluid transfer means and to the transfer means; a second means for shielding the second end of the fluid transfer means, having a body that is bound to the first means for shielding the fluid transfer means and to the transfer means.

The preferred embodiment for the fluid transfer device 29 is a hollow needle having a first 34 and second beveled end 35. The material for the hollow needle should be, but is not limited to, stainless steel. The method for making such a hollow needle with beveled ends is well known in the art. The hollow needle will be bound to the first and second means for shielding the first and second beveled ends. In this embodiment, the means for shielding the first beveled end 34, a first needle shield 36, will be similar to the conventional needle holder described earlier, being made of a plastic, and having the shape of a hollow cylinder. The first needle shield 36 will have an open end to accommodate a collection vessel 7,23 and a closed end, perforated by the hollow needle.

Figure 17:
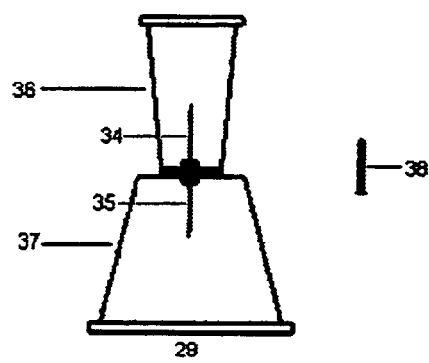
FIG. 17—This is a side view of the transfer device with the rubber sleeve removed from the first end of the transfer needle.
Figure 18:
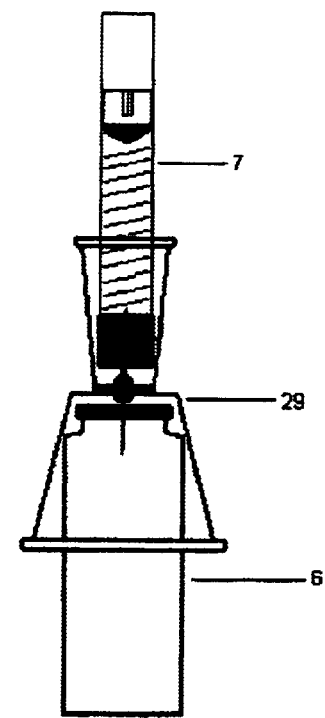
FIG. 18—This is a side view of the transfer device of FIG. 17, showing the device engaged to an evacuated culture bottle and the collection vessel of FIG. 5 with the plunger lock removed to allow for adequate transfer.
Figure 19:
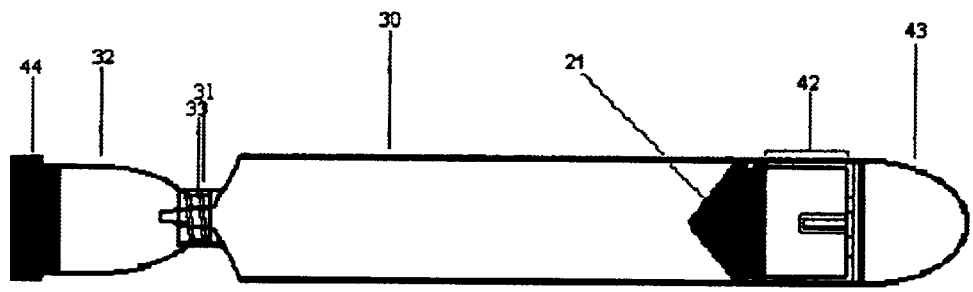
FIG. 19—This is a side view of the third embodiment of the collection vessel.
Figure 20:
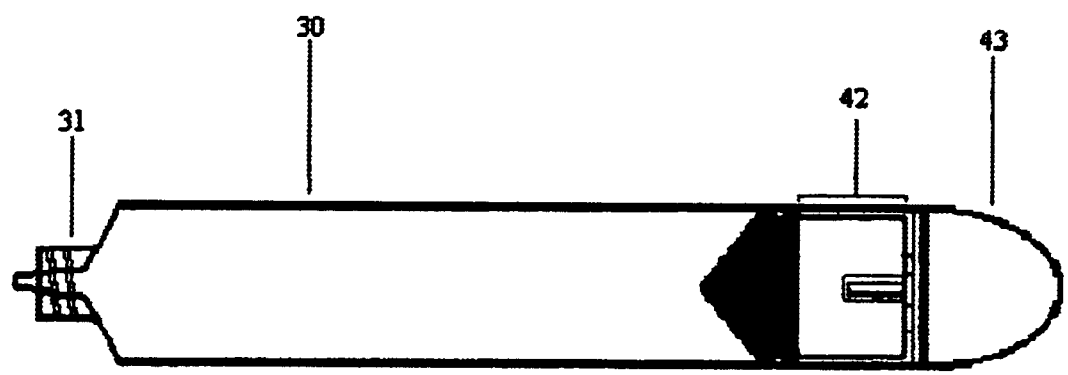
FIG. 20—This is a side view of the first section of the third embodiment of the collection vessel of FIG 19.
Figure 21:
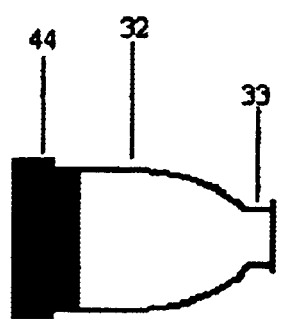
FIG. 21—This is a side view of the second section or adapter of the third embodiment of the collection vessel of FIG. 19.
Figure 22:
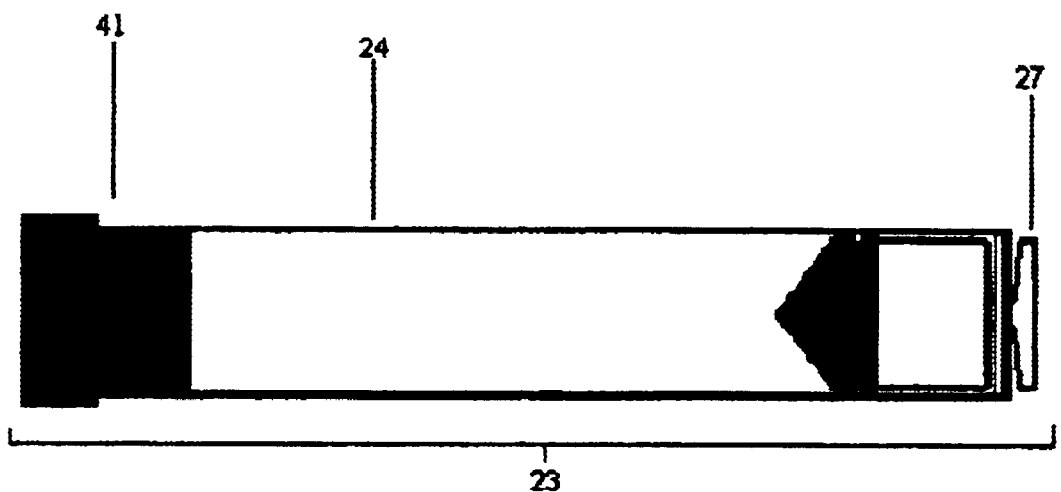
FIG. 22—This is a side view of the second embodiment of the collection vessel.
Figure 23:
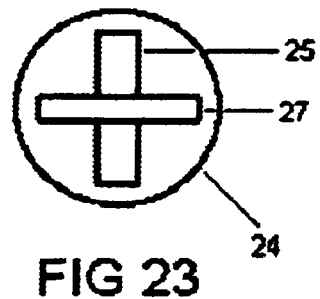
FIG. 23—This is a view of the third embodiment of the collection vessel of FIG. 22, turned to show the plunger lock held in place at the partially enclosed end.
Figure 24:
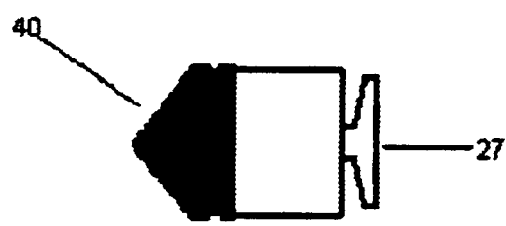
FIG. 24—This is a side view of the plunger of second embodiment of the collection vessel of FIG. 23.
Figure 25:
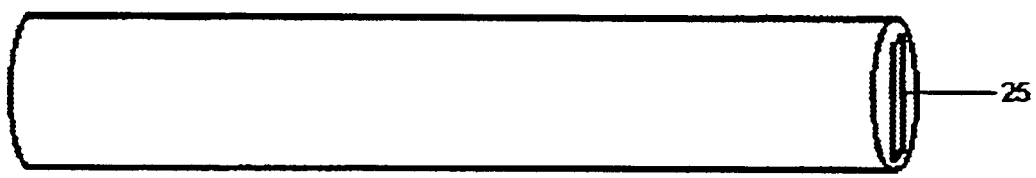
FIG. 25—This is a perspective view of the body of the second embodiment of the collection vessel of FIG. 23, turned to display the rectangular opening.

The means for shielding the second beveled end 35, the second needle shield 37, will have will have an open end to accommodate the evacuated culture vessel 6 and a closed end perforated by the hollow needle. The dimensions of the second needle shield 37 may vary to allow the second needle shield to accommodate various types of evacuated culture vessels. The second needle shield 37 illustrated in FIGS. 17,18 is configured to accommodate an evacuated culture tube with a larger diameter, but many other dimensions for the second needle shield 37 may be suitable and this disclosure should not be construed to limit the possible dimensions to those described. The first beveled end 34 is covered with a rubber sleeve 38 that will prevent gas from entering the evacuated culture vessel 6 when it is engaged with the transfer device 29 before the collection vessel 7,23. The presence of the rubber sleeve 38 is preferred because the premature entry of gas into the evacuated culture vessel 6 would result in loss of considerable vacuum, thereby preventing adequate transfer of the second body fluid specimen.

The transfer device suitable for transferring the second body fluid specimen from the third embodiment of the collection vessel 28 must be capable of attaching to a luer-type lock and penetrating the stopper of an evacuated culture vessel. One device suitable for transferring the second body fluid specimen from the third embodiment of the collection vessel 28 to an evacuated culture vessel is a transfer needle having a male luer-type fitting and a hollow needle for piercing materials. This type of transfer device will be used in a method of transfer to be described later. Other types of transfer devices are suitable for transferring the second body fluid specimen from the third embodiment collection vessel 28 to an evacuated culture vessel, and this disclosure should not be construed to limit the transfer device to those listed.

All of the devices described above are to be used in one of the methods for collecting a body fluid specimen described below. The methods require the following steps in order to collect a body fluid specimen for diagnostic testing i.e, blood culturing:

a. preparing a site for puncture using an antiseptic;
b. piercing the prepared puncture site using the fluid collection needle;
c. collecting the first body fluid specimen using the device for collecting the first body fluid specimen;
d. collecting the second body fluid specimen using the device for collecting the second body fluid specimen and;
e. selecting the second body fluid specimen for diagnostic testing of the kind that detects the presence of organisms in the specimen.

The antiseptics used to prepare the puncture site must be capable of eliminating an adequate quantity of contaminants from the puncture site. As used herein the phrase, "eliminating an adequate quantity of contaminants", means to prevent inclusion of a sufficient amount of contaminants in the body fluid specimen to be cultured. In this case, antiseptics would aid in preventing inclusion of a sufficient amount of contaminants in the body fluid specimen by rendering the contaminants non-viable, thus reducing the ability of included contaminants to contaminate.

One suitable antiseptic is isopropyl alcohol contained on a swab or pad. Isopropyl alcohol is a commonly used antiseptic in the art and in the method of collecting a body fluid specimen. If the method for collecting a body fluid specimen is successful in eliminating an adequate quantity of contaminants, then it is preferred that this is the only antiseptic used to prepare the puncture site. However, the ability of this method to eliminate an adequate quantity of contaminants has not yet been properly established by research. Therefore, alternate antiseptics may be required to prepare the puncture site and eliminate an adequate quantity of contaminants when used in the preferred embodiments of the methods to be described.

Other types of antiseptics suitable for preparing the puncture site in this method include iodophors, iodine tinctures, and chlorhexidine. Processes for manufacturing and methods of using these antiseptics are well known in the prior art. In the prior art, these antiseptics are used, in some cases with isopropyl alcohol, in the preparation punctures sites to reduce contamination. The use of these types of antiseptics is preferable in the event that research suggests that the method is more effective at eliminating an adequate quantity of contaminants when practiced with these antiseptics. Other types of antiseptics may be suitable for this method and this disclosure should not be construed to limit the antiseptic to those listed.

A first preferred embodiment of the method for collecting a body fluid specimen is described here, comprising the steps of:

a. preparing the site for puncture using an antiseptic;
b. piercing the prepared puncture site using the winged collection set/luer adapter/conventional needle holder assembly;
c. collecting the first body fluid specimen using the sterile evacuated specimen tube;
d. collecting the second body fluid specimen using the evacuated culture vessel.

The step of preparing the puncture site may use any one or a combination of the antiseptics listed, but as explained earlier must be capable of aiding in the elimination of an adequate quantity of contaminants.

In this embodiment, the winged collection set/luer adapter is assembled with the conventional needle holder to form an assembly for piercing the prepared puncture site. However, the use of this assembly is only appropriate when an evacuated culture vessel having a neck that is reduced in diameter is used to collect the second body fluid specimen. Some types of evacuated culture vessels have a larger neck diameter and require an adapter cap having a large enough diameter to accommodate the evacuated culture vessel. This adapter cap is similar to the second needle shield illustrated in FIGS. 17,18. These adapter caps also have means for accommodating smaller sized vessels. In an alternate embodiment, the adapter cap using its means for accommodating a smaller sized vessel assembled to the winged collection set and luer adapter will be used to pierce the puncture site.

The first body fluid specimen is collected by piercing the stopper of the sterile evacuated specimen tube using the needle of the luer adapter while the piercing needle of the winged collection set is in communication with a source of body fluid. The step of the of collecting the first body fluid specimen prior to collecting the second body fluid specimen, which will be cultured, is to ensure elimination of an adequate quantity of contaminants. This technique is referred to herein as "contaminant redirection". Contaminant redirection is necessary because it prevents the negative effects of improper antisepsis and puncture site re-palpation. This reduces waiting time, especially versus povidone-iodine, and makes the method less vulnerable to blood collector error.

Contaminant redirection is the most important feature of these methods. It provides a much more reliable method for piercing the skin of a patient, reducing the need to reattempt collection, and should eventually significantly reduce costs associated with culture contamination.

In this embodiment, the second body fluid specimen will be collected by piercing through the stopper of the evacuated culture vessel using the needle of the luer adapter. This embodiment is preferred as it has fewer steps than the embodiments described later, however, this method will not deal with blood specimen volume irregularity, as is discussed in the prior art In addition, the method also uses the winged collection set/luer adapter assembly only. This is not only somewhat less convenient, but given the cost of this assembly is roughly 9–10 fold greater than the cost of the fluid collection needle, the lack of versatility can increase the cost of collection considerably.

A second preferred embodiment of the method for collecting a body fluid specimen is described here, comprising the steps of:
a. preparing the site for puncture using an antiseptic;
b. piercing the prepared puncture site using the fluid collection needle;
c. collecting the first body fluid specimen using the sterile evacuated specimen tube;
d. collecting the second body fluid specimen using the evacuated specimen tube having an SPS additive;
e. transferring the second body fluid specimen using a conventional syringe/transfer needle assembly to an evacuated culture tube.

As with the first embodiment, the step of preparing the puncture site may use any one or a combination of the antiseptics listed, but as explained earlier must be capable of aiding in the elimination of an adequate quantity of contaminants. The step of piercing the skin the puncture site may use any of the listed devices for piercing the puncture site. This embodiment also uses contaminant redirection as described earlier.

The step of collecting the second body fluid specimen uses the evacuated specimen tube having the SPS additive described earlier. The second body fluid specimen will be collected by piercing through the stopper of the SPS additive evacuated specimen tube with the second end of the fluid collection needle or the needle of the luer adapter while the needle of the winged collection set or the first needle of the fluid collection needle is in communication with the source of body fluid.

The second body fluid must then be transferred from the SPS additive evacuated specimen tube to an evacuated culture vessel using the conventional syringe/transfer needle assembly. A step of sterilizing the contact surface of the SPS additive specimen tube may precede the step of transferring the second body fluid specimen. The transfer needle of the syringe/transfer needle assembly will then be used to pierce the stopper of the SPS additive specimen tube. The plunger of the syringe will then be retracted in order to transfer the second body fluid specimen to the syringe. The transfer needle will then be used to pierce the stopper of the evacuated culture vessel, thereby transferring the second body fluid specimen. It is important to note that because many evacuated culture vessels contain SPS in the liquid media, this and any embodiments using an SPS additive in its vessels to preserve the specimen for transport and transfer to an evacuated culture vessel should use an evacuated culture vessel that does not contain the SPS additive.

This method is preferred because it provides a means for monitoring the volume of body fluid transferred to the evacuated culture vessel. This method is preferable due to difficulties in monitoring the inoculating volume when blood is drawn directly into the evacuated culture vessels, as discussed in the prior art discussion. In addition, this method permits transfer of the second body fluid specimen at a designated workstation preferably at the laboratory and by a person other than the blood collector. This should provide a more fastidious sterilization of the contact surfaces prior to inoculation as well as a checkpoint at which the inoculating volume may be verified.

A third, fourth, and fifth embodiment of the method for collecting a body fluid specimen is described here, comprising the steps of:
a. preparing the site for puncture using an antiseptic;
b. piercing the prepared puncture site using the fluid collection needle;
c. collecting the first body fluid specimen using the sterile evacuated specimen tube;
d. collecting the second body fluid specimen using an embodiment of the collection vessel;
e. transferring the second body fluid specimen to the evacuated culture vessel using the transfer device.

As with the first two embodiments, the step of preparing the puncture site may use any one or a combination of the antiseptics listed, but as explained earlier must be capable of aiding in the elimination of an adequate quantity of contaminants. The step of piercing the skin the puncture site may use any of the listed devices for piercing the puncture site. These embodiments also use contaminant redirection as described earlier.

In the third method embodiment, the second body fluid specimen is collected by piercing through the stopper of the first embodiment collection vessel 7 with the second end of the fluid collection needle or the needle of the luer adapter while the needle of the winged collection set or the first end of the fluid collection needle is in communication with the source of body fluid.

In the third embodiment, the second body fluid specimen will be transferred using the transfer device 29 having a transfer needle with a first 34 and second beveled end 35 and a first 36 and second 37 needle shield, the first beveled end 34 having a rubber sleeve 38. Preferably, a step of sterilizing the contact surfaces of the collection vessels, in the first two collection vessel embodiments 7,23, and the stopper's of the evacuated culture vessels 6 using isopropyl alcohol will precede transfer of the second body fluid specimen.

The plunger lock 17 of the first collection vessel embodiment must be removed to allow the plunger 13 to move towards the open end. The second beveled end 35 of the transfer device will then be used to pierce the stopper of the evacuated culture vessel, the rubber sleeve 38 prevents gas from entering the culture vessel which would neutralize the vacuum in the vessel. The first beveled end 34 of the transfer needle will then be used to pierce the stopper 14 of the collection vessel, thus transferring the second body fluid specimen.

In the fourth embodiment, the second body fluid specimen is collected by piercing through the stopper of the second embodiment for a collection vessel 23 with the second end of the fluid collection needle or the needle of the luer adapter while the needle of the winged collection set or the first end of the fluid collection needle is in communication with the source of body fluid. Transfer of the second body fluid specimen in the fourth embodiment is similar to the transfer method in the third embodiment. However, in this embodiment, a step of rotating the T-shaped lock 17 of the plunger in order that the lock 17 and plunger can move through the rectangular opening 25 towards the open end is required.

In the fifth embodiment, the second body fluid specimen is collected by piercing through the stopper of the third embodiment for a collection vessel 28 with the second end of the fluid collection needle or the needle of the luer adapter while the needle of the winged collection set or the first end of the fluid collection needle is in communication with the source of body fluid. Transfer of the second body fluid specimen in the fifth embodiment uses the transfer needle as the transfer device. In this embodiment, the adapter must be removed and the male luer-type fitting of the transfer needle will be threaded into the female luer-type fitting 31 of the collection vessel. The plunger lock 43 is removed and the transfer needle will be used to pierce the stopper of the 43 culture vessel, thereby transferring the second body fluid specimen.

These embodiments do not require the conventional syringe/transfer needle to provide adequate transfer of the collection vessel contents as is necessary in the second embodiment of the method. As used herein the phrase "adequate transfer" means to transfer essentially all of the contents of a vessel to another vessel. The removal of the conventional syringe/transfer needle intermediate is advantageous because this step (e) of the second method embodiment is relatively more prone to needle sticks, blood splatter, and specimen contamination. This is because pulling back on the plunger of the conventional syringe to transfer the second body fluid specimen from the SPS additive evacuated specimen tube to the conventional syringe requires maintaining the plunger at one end of the conventional syringe against a relatively strong force provided by the lowered pressure within the SPS tube. In this state, loss of grip on the plunger can result in transferring the second body fluid specimen back to the SPS tube quickly, which is a less precarious occurrence resulting in only hemolysis of the sample. However, depending upon the type of transfer needle used, loss of grip can result in accidental needle sticks or forming of a body fluid vapor, both of which can result in illness for the blood collector.

In these method embodiments, the collection vessel embodiments are required because use of a conventional evacuated specimen tube such as those described in place of the first two collection vessel embodiments 7,23 to transfer the second body fluid specimen using the preferred embodiment for a transfer device results in inadequate transfer. This is due to an inability of the conventional evacuated specimen tube to relieve pressure during transfer. The lowering pressure within the evacuated specimen tube during transfer to the evacuated culture vessel causes a substantial amount of the second body fluid specimen to be retained in the tube. This problem could be overcome using a relatively large evacuated specimen tube of roughly a 20–25 ml capacity, evacuated such that the filling volume is 10 ml, or by using an evacuated tube of standard size 5–10 ml, but having a filling volume of only roughly 1–3 ml. However, this modified specimen tube would have to be unreasonably long in order to be accommodated by a conventional needle holder, or would not have sufficient volume to be effective. In contrast, the collection vessel embodiments use a movable plunger that is exposed to atmospheric pressure to increase the pressure gradient between a prepared collection vessel and the evacuated culture vessel. This allows the dimensions of the collection vessel embodiments to be reasonable thus allowing for convenient collection, transport, and transfer.

These embodiments can also use any of the listed devices for piercing the puncture site, thus saving cost. In addition, as described in the second embodiment, these embodiments promote regularity of the body fluid specimen volume as well as use the described technique of contaminant redirection.

It is also preferred that the described embodiments of the methods for collecting a body fluid specimen be performed using kits for collecting a body fluid specimen comprising:
a. the device for collecting the first body fluid specimen;
b. the device for collecting the second body fluid specimen;

These kits are assembled, sterilized, and packaged to maintain sterility using processes well known in the prior art. These kits are preferable because the devices for collecting the first and second body fluid specimens are included in a single container, thereby eliminating the need for the collector to assemble the necessary elements in order to collect the body fluid specimen. These kits are also preferable because they allow for simultaneous sterilization of the kit contents prior to, during, or after packaging. This satisfies the requirement for a device for collecting a first body fluid specimen that does not contaminate the device for piercing the puncture site as well as the requirement for a device for collecting the second body fluid specimen that does not contaminate the device for piercing the puncture site. Instruction for collecting the body fluid specimen may also be written on or included within the container to assist in teaching the methods. The kit for collecting a body fluid specimen may further comprise antiseptics, devices for piercing puncture sites, and transfer devices.

The first preferred embodiment of a kit for collecting a body fluid specimen comprises:
a. the sterile evacuated specimen tube and;
b. the first embodiment of the collection vessel 7.

The second preferred embodiment of a kit for collecting a body fluid specimen comprises:

a. the sterile evacuated specimen tube and;
b. the second embodiment of the collection vessel 23.

The third preferred embodiment of a kit for collecting a body fluid specimen comprises:
a. the sterile evacuated specimen tube and;
b. the third embodiment of the collection vessel 28.

The fourth preferred embodiment of a kit for collecting a body fluid specimen comprises:
a. the sterile evacuated specimen tube and;
b. the evacuated culture vessel.

The fifth preferred embodiment of a kit for collecting a body fluid specimen comprises:
a. the sterile evacuated specimen tube and;
b. the evacuated specimen tube comprising an SPS additive.

All of the preferred embodiments described herein assist in providing a method for collecting a body fluid specimen that is less prone to collector error. Variations and modification of the described embodiments will become apparent to those skilled in the art, without parting from the scope and spirit of this disclosure. For instance, an additive of saponin and polypropylene glycol in addition to SPS would allow a second body fluid specimen of blood to be used in lysis-centrifugation methods of culturing.

What is claimed is:

1. A collection vessel for collecting and transferring a body fluid specimen comprising: a hollow body having a first and a second end; a first seal at said first end; a plunger disposed within said hollow body between said first end and said second end; said plunger providing a second seal; a plunger lock coupled to said plunger; said plunger lock being configured to selectively maintain said plunger at said second end when at least a portion of said hollow body between said first seal and said second seal is at least partially evacuated; said plunger lock further configured to release said plunger, thereby allowing said plunger to move toward said first seal within said hollow body.

2. A collection vessel for collecting and transferring a body fluid specimen according to claim 1, further comprising: an airtight junction that interrupts said hollow body forming a first section and a second section; said first section having said first seal; said second section having said plunger and said plunger lock; said airtight junction configured to allow for separation of said first and said second section and coupling of a transfer needle to said second section.

3. A collection vessel for collecting and transferring a body fluid specimen according to claim 1, wherein said hollow body has the shape of a hollow cylinder.

4. A collection vessel for collecting and transferring a body fluid specimen according to claim 1, wherein said plunger lock comprises a threaded shaft and said plunger comprises a threaded receiver.

5. A collection vessel for collecting and transferring a body fluid specimen according to claim 1, wherein said plunger lock breaks away from said plunger, thereby allowing said plunger to move towards said first seal within said hollow body.

6. A collection vessel for collecting and transferring a body fluid specimen according to claim 1, wherein said plunger lock remains at least in part with said plunger as it moves toward said first seal within said hollow body.

7. A collection vessel for collecting and transferring a body fluid specimen according to claim 1, further comprising an additive within said collection vessel.

8. A collection vessel for collecting and transferring a body fluid specimen according to claim 1, wherein said collection vessel is sterilized and packaged to maintain sterility.

9. A method for collecting a first body fluid specimen and a second body fluid specimen, said second body fluid specimen having a lower concentration of living contaminants than said first body fluid specimen comprising the steps of: providing a fluid collection needle having a first end and a second end; providing a sterile evacuated specimen tube comprising a sterile hollow body having an open end, a sterile seal at said open end of said sterile evacuated specimen tube, said sterile seal of said sterile evacuated specimen tube configured wherein said sterile seal of said sterile evacuated specimen tube is maintained at said open end of said sterile evacuated specimen tube when at least a portion of said sterile hollow body of said sterile evacuated specimen tube is at least partially evacuated; providing a device for collecting a second body fluid specimen comprising a sterile hollow body having an open end, a sterile seal at said open end of said device for collecting a second body fluid specimen, said sterile seal of said device for collecting a second body fluid specimen configured wherein said sterile seal of said device for collecting a second body fluid specimen is maintained at said open end of said device for collecting a second body fluid specimen when at least a portion of said sterile hollow body is at least partially evacuated; providing an antiseptic; preparing a site on a patient's skin for puncture using said antiseptic; piercing said site using said first end of said fluid collection needle; at least partially filling said sterile evacuated specimen tube with said first body fluid specimen by piercing through said sterile seal of said sterile evacuated specimen tube using said second end of said fluid collection needle such that piercing through said sterile seal of said sterile evacuated specimen tube does not contaminate said second end of said fluid collection needle; at least partially filling said device for collecting said second body fluid specimen with said second body fluid specimen having fewer living contaminants than said first body fluid specimen by piercing through said sterile seal of said device for collecting a second body fluid specimen using said second end of said fluid collection needle, such that piercing through said sterile seal of said device for collecting a second body fluid specimen does not contaminate said second end of said fluid collection needle and; selecting said second body fluid specimen for use in a diagnostic test to detect the presence of organisms in said second body fluid specimen.

10. A method for collecting a first body fluid specimen and a second body fluid specimen, said second body fluid specimen having a lower concentration of living contaminants than said first body fluid specimen according to claim 9, wherein said device for collecting a second body fluid specimen is an evacuated culture vessel further comprising a liquid media contained within said sterile hollow body of said device for collecting a second body fluid specimen.

11. A method for collecting a first body fluid specimen and a second body fluid specimen, said second body fluid specimen having a lower concentration of living contaminants than said first body fluid specimen according to claim 9, wherein said device for collecting a second body fluid specimen is an evacuated specimen tube further comprising an additive of sodium polyanethole sulfonate within said sterile hollow body of said device for collecting a second body fluid specimen.

12. A method for collecting a first body fluid specimen and a second body fluid specimen, said second body fluid specimen having a lower concentration of living contaminants than said first body fluid specimen according to claim 9, wherein said device for collecting a second body fluid specimen is a collection vessel further comprising: said sterile hollow body of said device for collecting a second body fluid specimen having a second end; a plunger disposed within said sterile hollow body of said device for collecting a second body fluid specimen between said open end of said device for collecting a second body fluid specimen and said second end; said plunger sealing said sterile hollow body of said device for collecting a second body fluid specimen; a plunger lock coupled to said plunger; said plunger lock being configured to selectively maintain said plunger at said second end when at least a portion of said sterile hollow body of said device for collecting a second body fluid specimen between said sterile seal of said device for collecting a second body fluid specimen and said plunger is at least partially evacuated; said plunger lock further configured to release said plunger, thereby allowing said plunger to move toward said sterile seal of said device for collecting a second body fluid specimen within said sterile hollow body of said device for collecting a second body fluid specimen.

13. A method for collecting a first body fluid specimen and second body fluid specimen, said second body fluid specimen having a lower concentration of living contaminants than said first body fluid specimen comprising the steps of: providing a fluid collection needle having a first end and a second end and a tube between said first end and said second end; providing a sterile evacuated specimen tube comprising a hollow body having an open end, a sterile seal at said open end of said sterile evacuated specimen tube, said sterile seal of said sterile evacuated specimen tube configured wherein said sterile seal of said sterile evacuated specimen tube is at said open end of said sterile evacuated specimen tube and said hollow body of said sterile evacuated specimen tube is at least partially evacuated, and configured wherein said sterile evacuated specimen tube is sterilized and packaged to maintain sterility; providing an evacuated culture vessel comprising a hollow body having an open end, a sterile seal at said open end of said evacuated culture vessel, a liquid media within said hollow body of said evacuated culture vessel, configured wherein said hollow body of said evacuated culture vessel is at least partially evacuated; providing an antiseptic; preparing a site on a patient's skin for puncture using said antiseptic; piercing said site on a patient's skin using said first end of said fluid collection needle; at least partially filling said sterile evacuated specimen tube with said first body fluid specimen by piercing through said sterile seal of said sterile evacuated specimen tube using said second end of said fluid collection needle; at least partially filling said evacuated culture vessel with said second body fluid specimen by piercing through said sterile seal of said evacuated culture vessel with said, second end of said fluid collection needle; using said evacuated culture vessel having said second body fluid specimen for a diagnostic test to detect the presence of organisms in said second body fluid specimen.

14. A method for collecting a first body fluid specimen and second body fluid specimen, said second body fluid specimen having a lower concentration of living contaminants than said first body fluid specimen comprising the steps of: providing a fluid collection needle having a first and a second end and a tube between said first end and said second end; providing a first sterile evacuated specimen tube comprising a sterile hollow body having an open end, a sterile seal at said open end of said first sterile evacuated specimen tube, said sterile seal of said first sterile evacuated specimen tube configured wherein said sterile seal of said first sterile evacuated specimen tube is maintained at said open end of said first sterile evacuated specimen tube when at least a portion of said sterile hollow body of said first sterile evacuated specimen tube is at least partially evacuated; providing a second sterile evacuated specimen tube comprising a sterile hollow body having an open end, a sterile seal of said second sterile evacuated specimen tube at said open end, an additive of sodium polyanetholesulfonate within said sterile hollow body of said second sterile evacuated specimen tube, said sterile seal of said second sterile evacuated specimen tube configured wherein said sterile seal of said second sterile evacuated specimen tube is maintained at said open end of said second sterile evacuated specimen tube when at least a portion of said sterile hollow body of said second sterile evacuated specimen tube is at least partially evacuated; providing an antiseptic; providing a transfer device comprising a syringe having a hollow body and a plunger, and a transfer needle, said syringe and said transfer needle configured wherein pulling back on said plunger allows a movement of fluid into said syringe through said transfer needle providing an evacuated culture vessel comprising a hollow body having an open end, a sterile seal at said open end of said evacuated culture vessel, a liquid media within said hollow body of said evacuated culture vessel, configured wherein said hollow body of said evacuated culture vessel is at least partially evacuated; preparing a site on a patient's skin for puncture using said antiseptic; piercing said site on a patient's skin using said first end of said fluid collection needle; at least partially filling said first sterile evacuated specimen tube with said first body fluid specimen by piercing through said sterile seal of said first sterile evacuated specimen tube using said second end of said fluid collection needle, such that said second end of said fluid collection vessel is not contaminated by said sterile seal of said first sterile evacuated specimen tube; at least partially filling said second sterile evacuated specimen tube with said second body fluid specimen by piercing through said sterile seal of said second sterile evacuated specimen tube using said second end said fluid collection needle, such that said second end of said fluid collection needle is not contaminated by said sterile seal of said second sterile evacuated specimen tube; transferring said second body fluid specimen to said evacuated culture vessel and; using said evacuated culture vessel having said second body fluid specimen for a diagnostic test to detect the presence of organisms in said second body fluid specimen.

15. A method for collecting a first body fluid specimen and second body fluid specimen, said second body fluid specimen having a lower concentration of living contaminants than said first body fluid specimen comprising the steps of: providing a fluid collection needle comprising a cannula having a first end and a second end, providing a sterile evacuated specimen tube comprising; a sterile hollow body having a open end, a sterile seal at said open end, said sterile seal configured wherein said sterile seal is maintained at said open end when at least a portion of said sterile hollow body is at least partially evacuated; providing a sterile collection vessel for collecting and transferring a body fluid specimen comprising a hollow body having a first end and second end, a first seal at said first end, a plunger disposed within said hollow body between said first end and said second end, said plunger providing a second seal, a plunger lock coupled to said plunger, said plunger, lock being configured to selectively maintain said plunger at said second end when at least a portion of said hollow body between said first seal and said second seal is at least partially evacuated, said plunger lock further configured to release said plunger thereby allowing said plunger to move toward said first seal within said hollow body; providing an antiseptic; providing a transfer device comprising a cannula having a first end and second end, said first end of said transfer device protected by a first needle shield, said second end of said transfer device protected by a second needle shield; providing an evacuated culture vessel comprising a hollow body having an open end, a sterile seal at said open end of said evacuated culture vessel, a liquid media within said hollow body of said evacuated culture vessel, configured wherein said hollow body of said evacuated culture vessel is at least partially evacuated; preparing a site on a patient's skin for puncture using said antiseptic; piercing said site on a patient's skin using said first end of said fluid collection needle; at least partially filling said sterile evacuated specimen tube with said first body fluid specimen by piercing through said sterile seal of said sterile evacuated specimen tube using said second end of said fluid collection needle, such that said second end of said fluid collection needle is not contaminated by said sterile seal of said sterile evacuated specimen tube; at least partially filling said collection vessel with said second body fluid specimen by piercing through said first seal of said collection vessel using said second end of said fluid collection needle, such that said second end of said fluid collection needle is not contaminated by said first seal of collection vessel; configuring said plunger lock to release said plunger; piercing through said first seal of said collection vessel using said first end of said transfer device; piercing through said sterile seal of said evacuated culture vessel, such that said second body fluid specimen flows into said evacuated culture vessel and; using said evacuated culture vessel having said second body fluid specimen for a diagnostic test to detect the presence of organisms in said second body fluid specimen.

16. A kit for collecting a first body fluid specimen and a second body fluid specimen, said second body fluid specimen having a lower concentration of living contaminants than said first body fluid specimen said kit comprising: a sterile evacuated specimen tube comprising a sterile hollow body having an open end, a sterile seal at said open end, said sterile seal configured wherein said sterile seal is maintained at said open end when at least a portion of said sterile hollow body is at least partially evacuated and; a collection vessel comprising a hollow body having a first end and second end, a first seal at said first end, a plunger disposed within said hollow body between said first end and said second end, said plunger providing a second seal, a plunger lock coupled to said plunger, said plunger lock being configured to selectively maintain said plunger at said second end when at least a portion of said hollow body between said first seal and said second seal is at least partially evacuated, said plunger lock further configured to release said plunger thereby allowing said plunger to move toward said first seal within said body.

17. A method for collecting a first blood specimen and second blood specimen, said second blood specimen having a lower concentration of living contaminants than said first blood specimen comprising the steps of: providing a blood collection needle having a first end and a second end; providing a collection kit comprising a sterile evacuated specimen tube having a sterile hollow body having an open end, a sterile seal at said open end of said sterile evacuated specimen tube, said sterile seal of said sterile evacuated specimen tube, configured wherein said sterile seal of said sterile evacuated specimen tube is maintained at said open end of said sterile evacuated specimen tube when at least a portion of said sterile hollow body of said sterile evacuated specimen tube is at least partially evacuated and a collection vessel comprising a hollow body having a first end and second end, a first seal at said first end of said collection vessel, a plunger disposed within said hollow body of said collection vessel between said first end of said collection vessel and said second end of said collection vessel, said plunger providing a second seal, a plunger lock coupled to said plunger, said plunger lock being configured to selectively maintain said plunger at said second end of said collection vessel when at least a portion of said hollow body of said collection vessel between said first seal and said second seal is at least partially evacuated, said plunger lock further configured to release said plunger thereby allowing said plunger to move toward said first seal within said hollow body of said collection vessel; providing an antiseptic; providing a transfer device comprising a cannula having a first end and second end, said first end of said transfer device protected by a first needle shield, said second end of said transfer device protected by a second needle shield; providing an evacuated culture vessel comprising a hollow body having an open end, a sterile seal at said open end of said evacuated culture vessel, a liquid media within said hollow body of said evacuated culture vessel, configured wherein said hollow body of said evacuated culture vessel is at least partially evacuated; opening said collection kit; preparing a site on a patient's skin for puncture using said antiseptic; piercing said site on a patient's skin using said first end of said blood collection needle; at least partially filling said sterile evacuated specimen tube with said first blood specimen by piercing through sterile seal of said first sterile evacuated specimen tube using said second end of said blood collection needle, such that said second end of said blood collection needle is not contaminated by said sterile seal of said sterile evacuated specimen tube; at least partially filling said collection vessel with said second blood specimen by piercing through said first seal of said collection vessel using said second end of said blood collection needle, such that said second end of said fluid collection needle is not contaminated by said first seal of said collection vessel; configuring said plunger lock to release said plunger; piercing through said first seal of said collection vessel using said first end of said transfer device; piercing through said sterile seal of said evacuated culture vessel, such that said second body fluid specimen flows into said evacuated culture vessel and; using said evacuated culture vessel having said second blood specimen for a diagnostic test to detect the presence of organisms in said second blood specimen.

* * * * *